United States Patent [19]
Wolf et al.

[11] Patent Number: 6,132,737
[45] Date of Patent: Oct. 17, 2000

[54] METHOD FOR REDUCING SUNBURN CELL FORMATION WITH COSMETIC COMPOSITIONS CONTAINING ASCORBIC ACID

[75] Inventors: Barbara Ann Wolf, Scardsdale, N.Y.; Patricia Beatrice Siuta, Mahwah, N.J.

[73] Assignee: Revlon Consumer Products Corporation, New York, N.Y.

[21] Appl. No.: 08/939,893

[22] Filed: Sep. 29, 1997

[51] Int. Cl.⁷ .............................. A61K 6/00; A61K 7/00
[52] U.S. Cl. ................. 424/401; 424/59; 424/63
[58] Field of Search ................ 424/47, 401, 59, 424/70, 63

[56] References Cited

U.S. PATENT DOCUMENTS

| | | | |
|---|---|---|---|
| 4,847,071 | 7/1989 | Bissett et al. | 424/47 |
| 4,869,897 | 9/1989 | Chatterjee et al. | 424/47 |
| 4,954,332 | 9/1990 | Bissett et al. | 424/59 |
| 5,140,043 | 8/1992 | Darr | 514/474 |
| 5,587,149 | 12/1996 | Punto | 424/59 |
| 5,609,875 | 3/1997 | Hadas | 424/195.1 |
| 5,622,690 | 4/1997 | Potter | 424/59 |
| 5,629,004 | 5/1997 | Hadas | 424/401 |

FOREIGN PATENT DOCUMENTS

| | | |
|---|---|---|
| 755674 | 1/1997 | European Pat. Off. . |
| 959145 | 4/1997 | Japan . |
| 9101744 | 10/1991 | WIPO . |
| 9418933 | 9/1994 | WIPO . |

OTHER PUBLICATIONS

Photodermatology vol. 4 pp. 127–134 1987 "The Sunburn Cell".

Photodermatology vol. 2 pp. 144–150 1985 "Miniature Swine as an Animal Model . . . ".

*Primary Examiner*—Thurman K. Page
*Assistant Examiner*—William E. Benston, Jr.
*Attorney, Agent, or Firm*—Julie Blackburn

[57] ABSTRACT

A method for reducing the formation of sunburn cells in mammalian skin exposed to ultraviolet radiation, comprising applying a cosmetic composition containing stabilized ascorbic acid to the the skin prior to exposure to ultraviolet radiation.

17 Claims, No Drawings

METHOD FOR REDUCING SUNBURN CELL FORMATION WITH COSMETIC COMPOSITIONS CONTAINING ASCORBIC ACID

TECHNICAL FIELD

The invention is in the field of using ascorbic acid to protect skin from generating sunburn cells in response to ultraviolet radiation.

BACKGROUND OF THE INVENTION

Exposure to ultraviolet (UV) radiation is known to provide a variety of undesirable effects such as photoaging and photodamage of the skin, and in more extreme cases, cutaneous squamous cell or basal cell carcinoma and malignant melanoma. UV radiation generally encompasses light in the wavelength range of 200–400 nm., with UVA having a wavelength of about 320–440 nm., UVB a wavelength of 290–320 nm., and UVC a wavelength of less than about 280 nm. Acute UV exposure causes solar erythema or sunburn, and is associated with formation of dyskeratotic cells (also called sunburn cells) in the epidermis. Sunburn cells are epidermal cells with an eosinophilic cytoplasm and either no nucleus or a contracted, irregular, nucleus, when stained with hematoxylin and eosin. The formation of sunburn cells is believed to indicate damage to cellular DNA by UV radiation, and in particular UVB radiation.

Traditional sunscreen compositions containing titanium dioxide and chemical sunscreens do provide some degree of protection against formation of sunburn cells. However, these products still permit formation of significant numbers of sunburn cells in skin which is exposed to UV radiation. U.S. Pat. No. 5,140,043 teaches that ascorbic acid containing compositions are capable of reducing sunburn cell formation in the skin of Yorkshire swine, however there is no indication of the effects of such compositions on human skin.

Most unexpectedly, it has been found that ascorbic acid containing compositions are capable of significantly reducing the formation of sunburn cells in mammalian skin when compared to placebo and untreated skin.

SUMMARY OF THE INVENTION

The invention is directed to a method for reducing the formation of sunburn cells in mammalian skin exposed to ultraviolet radiation, comprising applying a cosmetic composition containing ascorbic acid to the the skin prior to exposure to ultraviolet radiation.

It has been found that a 10–95% reduction in the number of sunburn cells can be achieved by treating mammalian skin with ascorbic acid containing compositions prior to exposure to UV radiation.

DETAILED DESCRIPTION

The invention comprises a method for reducing the formation of sunburn cells in mammalian, particularly human, skin exposed to UV radiation by applying ascorbic acid containing compositions to the skin prior to exposure to UV radiation.

The Ascorbic Acid Containing Compositions

Preferably the ascorbic acid used in the compositions is L-ascorbic acid although derivatives thereof may also be suitable, such as esters and salts of ascorbic acid, or protein bound forms. Generally, the compositions used in the method of the invention contain about 0.01–25%, preferably 1–20%, more preferably 5–18% by weight of the total composition of ascorbic acid.

The compositions may be cosmetic or pharmaceutical compositions, and may exist in a wide variety of forms, such as emulsions, suspensions, solutions and the like. Preferably the compositions are in the form of lotions, creams, and other types of cosmetic compositions.

The ascorbic acid compositions used in the method of the invention may be those set forth in U.S. Pat. No. 5,629,004, which is hereby incorporated by reference. Such compositions are emulsions containing stabilized ascorbic acid in a water in oil emulsion wherein the aqueous phase contains stabilized ascorbic acid and has a pH of less than or equal to 3.5, and the emulsifying agent is dimethicone copolyol or an alkyldimethicone copolyol. The compositions preferably contain about 0.5 to 5% by weight of the total composition of ascorbic acid dissolved in the aqueous phase, about 1–10% by weight of the emulsifying agent, about 65–75% by weight of an aqueous phase, and the remainder an oil phase, and have a pH of about 1.5 to 3.5.

Also suitable for use in the method of the invention are topical application emulsions of ascorbic acid disclosed in U.S. Pat. No. 5,587,149, which is hereby incorporated by reference. The emulsions disclosed therein are anhydrous emulsions having ascorbic acid dissolved in a polyethylene glycol solvent dispersed in an oil phase. The anhydrous emulsions are placed in soft gelatin capsules which are opened by the consumer and applied to the skin.

Ascorbic acid containing compositions such as those disclosed in Japanese publication Hei 9-59145 are also suitable for use in the method of the invention. These compositions are liquid formulations having a pH of about 2 to 5, and containing ascorbic acid, a cane sugar fatty acid ester and a phospholipid. The cane sugar fatty acid esters are obtained by esterifying cane sugar with a fatty acid having 12 to 22 carbon atoms. The phospholipid is, preferably, a glycerophospholipids, in particular lecithin.

The ascorbic acid containing compositions disclosed in European Patent Application EP 0 755 674, are also suitable for use in the method of the invention. These compositions have a water activity value of about 0.85 or less, and are aqueous emulsions containing ascorbic acid dissolved in a polyol. Preferably, these compositions contain, by weight of the total composition, of about 0.5–10% ascorbic acid, 5–40% oil, and 30–99.9%, and a certain minimum level of water.

Also suitable are the compositions disclosed in U.S. Pat. No. 5,140,043, which is hereby incorporated by reference. These aqueous compositions contain greater than about 1% w/v ascorbic acid, and have a pH of less than about 3.5. The compositions may contain various glycols, oils, and the like.

Particularly preferred for use in the method of the invention are ascorbic acid compositions disclosed in Case Docket No. Rev 96-9, filed Jun. 27, 1997 as U.S. Ser. No. 883,671, entitled "Compositions Containing Stabilized Ascorbic Acid and Related Methods", by inventors Teanoosh Moaddel, William Radice, Barbara Wolf, and Bernadette Guthauser. The compositions disclosed therein are in the form of an anhydrous emulsions having as a dispersed phase, ascorbic acid dissolved in a nonaqueous polar organic solvent, and as the continuous phase, phase, a nonaqueous nonpolar organic solvent; or in the alternative, anhydrous emulsions having as the dispersed phase, a nonaqueous nonpolar organic solvent, and as the continuous phase ascorbic acid dissolved in a nonaqueous polar organic solvent. Preferably the compositions contain about 0.1–50% ascorbic acid, 5–98% of a nonaqueous polar organic solvent, and 5–98% of a nonaqueous nonpolar organic solvent.

A variety of nonaqueous polar organic solvents suitable for use in the dispersed phase of the anhydrous emulsion. As mentioned above, a solvent, in particular a nonaqueous solvent, is considered "polar" in the context of the invention if the logarithm of the partition coefficient of the solvent is less than or equal to −0.2 at room temperature. Examples are as follows.

Polyols

Polyols are suitable nonaqueous polar organic solvents. For purposes of this specification, polyols are defined as compounds which contain three or more hydroxyl groups per molecule. Examples of suitable polyols include fructose, glucamine, glucose, glucose glutamate, glucuronic acid, glycerin, 1,2,6-hexanetriol, hydroxystearyl methylglucamine, inositol, lactose, malitol, mannitol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, riboflavin, sorbeth-6, sorbeth-20, sorbeth-30, sorbeth-40, sorbitol, sucrose, thioglycerin, xylitol, and mixtures thereof. An especially preferred polyol is glycerin.

Polymeric or Monomeric Ethers

Also suitable as the nonaqueous polar organic solvent are homopolymeric or block copolymeric liquid ethers. Polymeric ethers are preferably formed by polymerization of monomeric alkylene oxides, generally ethylene or propylene oxides. Preferred monomeric ethers are those exhibiting the structure below were n=1. Preferred polymeric ethers exhibit the general structure below wherein n=2 to 20:

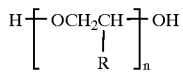

where R is H or $C_{1-10}$ straight or branched chain alkyl, and n is 1 to 20. Examples of such polymeric ethers include PEG, PPG, and derivatives thereof.

Other examples of suitable polymeric ethers include polyoxypropylene polyoxyethylene block copolymers having the general formula:

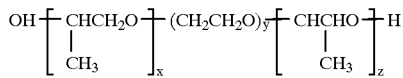

wherein x is 1–200, y is 1–200 and z is 1–200. Such compounds are sold under the CTFA name Meroxapol 105, 108, 171, 172, 174, 178, 251, 252, 254, 255, 258, 311, 312, and 314.

Mono- and Dihydric Alcohols

Also suitable for use as to the nonaqueous polar organic solvent are mono- and dihydric alcohols of the general formula $R(OH)_n$ where n is 1 or 2 and R is a substituted or unsubstituted saturated $C_{2-10}$, preferably $C_{1-8}$ alkyl, or a substituted or unsubstituted alicyclic, bicyclic, or aromatic ring, with the substituents selected from halogen, alkoxy, hydroxy, and so on. Examples of suitable alcohols include monohydric alcohols such as ethanol, isopropanol, hexyldecanol, benzyl alcohol, propyl alcohol, and isopropyl alcohol, as well as dihydric alcohols such as hexylene glycol, diethylene glycol, ethylene glycol, propylene glycol, 1,2-butylene glycol, triethylene glycol, dipropylene glycol, and mixtures thereof.

Sorbitan Derivatives

Sorbitan derivatives, which are defined as ethers or esters of sorbitan, are also suitable polar solvents. Examples of suitable sorbitan derivatives are the Polysorbates, which are defined as stearate esters of sorbitol and sorbitan anhydrides, such as Polysorbate 20, 21, 40, 60, 61, 65, 80, 81, and 85. Also suitable are fatty esters of hexitol anhydrides derived from sorbitol, such as sorbitan trioleate, sorbitan tristearate, sorbitan sesquistearate, sorbitan stearate, sorbitan palmitate, sorbitan oleate, and mixtures thereof.

Other nonaqueous polar solvents will also work in the claimed compositions, provided the logarithm of the measured partition coefficient of the solvent is less than −0.2 at room temperature.

The anhydrous emulsions used in the preferred embodiment of the invention contain about 1–99%, preferably 20–80%, more preferably 40–60%, by weight of total composition, of a nonaqueous nonpolar organic solvent as the continuous phase. Such solvents are defined as those where the logarithm of the partition coefficient is greater than −0.2 at room temperature. A variety of nonaqueous nonpolar organic solvents can be used in the compositions of the invention.

Silicones

Silicones are suitable nonpolar compounds. The silicones may be volatile or non-volatile. The term "volatile" means that the silicone has a measureable vapor pressure, i.e. a vapor pressure of at least 2 mm. of mercury at 20° C. If volatile, the silicone generally will have a viscosity of 0.5 to 25 centistokes at 25° C. Suitable volatile silicones include cyclic silicones, linear silicones, or mixtures thereof. Cyclic silicones (or cyclomethicones) are of the general formula:

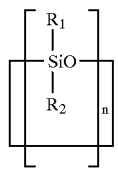

wherein n=3–7, and $R_1$ and $R_2$ are each independently H, $C_{1-8}$ alkyl, aryl, aralkyl, alkenyl, or a cylic or alicylic ring. Preferably $R_1$ and $R_2$ are each independently H or $CH_3$. Most preferably $R_1$ and $R_2$ are each $CH_3$.

Linear volatile silicones in accordance with the invention have the general formula:

$(CH_3)_3Si-O-[Si(CH_3)_2-O]_n-Si(CH_3)_3$ where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

The silicone may also be nonvolatile, and in particular water insoluble nonvolatile silicones. The term "nonvolatile" means that the silicone has a vapor pressure of less than 2 mm. of mercury at 20° C. A variety of silicones fit this definition including dimethicone, phenyl trimethicone, diphenyl dimethicone, methicone, hexadecyl methicone, stearoxydimethicone, stearyl dimethicone, cetyl dimethicone, and so on.

Cyclomethicone is the preferred silicone for use in the compositions of the invention.

Esters

In addition to the sorbitan esters, other esters are also suitable as the nonaqueous nonpolar organic solvent. In general such esters have the formula RCO—OR wherein each R is independently a $C_{1-25}$ straight or branched chain saturated or unsaturated alkyl, alkylcarbonyloxyalkyl, or alkoxycarbonylalkyl, aryl, which may be substituted or unsubstituted with halogen, hydroxyl, alkyl, and the like.

Examples of suitable esters include alkyl acetates, alkyl behenates, alkyl lactates, alkyl benzoates, alkyl octanoates, alkyl salicylates, and in particular $C_{12-15}$ alkyl benzoate. Examples of further esters are set forth on pages 502–506 of the CTFA Cosmetic Ingredient Handbook, Second Edition, 1992, which is hereby incorporated by reference.

Fats and Oils

Fats and oils are also suitable as the nonaqueous nonpolar organic solvent. Preferably these materials are liquids or semi-solids at room temperature. They are generally defined as glyceryl esters of fatty acids (triglycerides), as well as the synthetically prepared esters of glycerin and fatty acids having the following general formula:

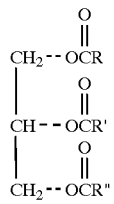

wherein R, R', and R" are each independently fatty acid radicals. Examples of such materials include oils such as apricot kernel oil, avocado oil, canola oil, olive oil, sesame oil, peanut oil, soybean oil, trilinolenin, trilinolein, trioctanoin, tristearin, triolein, sesame oil, rapeseed oil, sunflower seed oil, and so on.

Fatty Acids

Fatty acids are also suitable as the nonaqueous nonpolar organic solvent in the compositions of the invention. Preferably the fatty acids are liquid or semi-solid at room temperature. Fatty acids are the carboxylic acids obtained by hydrolysis of animal or vegetable fats and oils. Carboxylic acids having alkyl chains shorter than about seven carbon atoms are not generally considered fatty acids. Fatty acids have the general structure R—COOH where R is a straight or branched chain saturated or unsaturated $C_{7-65}$ alkyl. Examples of suitable fatty acids include arachidic acid, arachidonic acid, behenic acid, capric acid, caproic acid, caprylic acid, coconut acid, corn acid, cottonseed acid, hydrogenated coconut acid, hydroxystearic acid, lauric acid, linoleic acid, linolenic acid, linseed acid, myristic acid, oleic acid, palmitic acid, palm kernel acid, soy acid, tallow acid, and the like.

Fatty Alcohols

Fatty alcohols may also be used as the nonaqueous nonpolar organic solvent. Fatty alcohols are generally made by reducing the fatty acid —COOH group to the hydroxyl function. They generally have the formula $RCH_2OH$. Examples of fatty alcohols are behenyl alcohol, $C_{9-11}$ alcohol, $C_{12-13}$ alcohol, $C_{12-15}$ alcohol, $C_{12-16}$ alcohol, caprylic alcohol, cetearyl alcohol, cetyl alcohol, coconut alcohol, decyl alcohol, lauryl alcohol, myristyl alcohol, oleyl alcohol, and the like.

Hydrocarbons

Hydrocarbons are also good nonaqueous nonpolar organic solvents in accordance with the invention. Examples of suitable hydrocarbons include $C_{7-60}$ isoparaffins, ethane, heptane, hexane, hydrogenated polyisobutene, isobutane, isododecane, isoeicosane, isohexadecane, isopentane, microcrystalline wax, mineral oil, mineral spirits, paraffin, petrolatum, petroleum distillates, squalene, polyethylene, and mixtures thereof. Preferred hydrocarbons are mineral oil and polyethylene.

Lanolin and Lanolin Derivatives

Also suitable as the nonaqueous nonpolar organic solvent are lanolin and derivatives thereof. Examples of such materials include acetylated hydrogenated lanolin, acetylated lanolin alcohol, laneth, lanolin acid, lanolin oil, lanolin alcohol, lanolin wax, and so on.

The compositions used in the preferred embodiment of the invention are made by first subjecting the nonaqueous polar organic solvent to an input of energy, preferably heat energy. In particular, the nonaqueous polar organic solvent is heated to a temperature sufficient to dissolve the ascorbic acid. A temperature above room temperature is generally required to achieve solubilization of ascorbic acid to any appreciable degree. Preferably, the nonaqueous polar organic solvent is heated to a temperature of about 70 to 170, more preferably about 80 to 120, more preferably about 90–110, and most preferably about 95–105° C. The heat energy required may depend on conditions such as the pressure at which the nonaqueous polar organic solvent is maintained. For example, if the pressure of the nonaqueous polar organic solvent is increased above standard pressure at room temperature, the temperature required to dissolve appreciable levels of ascorbic acid in the solvent is correspondingly less. Conversely, if the nonaqueous polar organic solvent is maintained at a pressure which is less than the standard pressure at room temperature, the temperature required to dissolve appreciable levels of ascorbic acid may be correspondingly greater. The energy source may be standard heat as well as heat radiation from sources such as long and short microwaves, infrared radiation, sonication, microfluidization, and the like.

While maintaining the temperature, the ascorbic acid is added to the nonaqueous polar organic solvent with stirring until dissolved. The temperature of the mixture is then reduced, i.e. the mixture is cooled, by reducing the temperature by 10 to 145° C., more preferably by 20 to 100° C., most preferably by 40 to 95° C. Most preferably the mixture is cooled to room temperature. It is preferred to cool the mixture to room temperature quickly, for example by plunging a container of the mixture into an ice water bath until the mixture attains room temperature.

In the preferred embodiment of the invention, one of the nonaqueous polar organic solvents is heated in a vessel to about 100° C. The ascorbic acid is added with stirring until dissolved. The vessel containing the mixture is then plunged into an ice water bath and held there until it has cooled to room temperature. Then, the mixture is reheated to a temperature of 70–170°, 80–110°, preferably 95–105°, more preferably about 100° C. and the second nonaqueous polar organic solvent is added with stirring. The mixture is then rapidly cooled to room temperature by putting it into an ice water bath.

It has been discovered that the rapid cooling appears to promote solubilization of the ascorbic acid into the nonaqueous polar organic solvent. In addition, adding the nonaqueous polar organic solvents one at a time followed by rapid cooling, promotes the highest level of stability and solubility of ascorbic acid in the nonaqueous polar organic solvent. Most unexpectedly, concentrations of solubilized ascorbic acid up to 25% have been achieved using solvents which normally provide very low solubility of ascorbic acid.

The ascorbic acid solubilized in the nonaqueous polar organic solvent is emulsified into the nonaqueous nonpolar organic solvent at room temperature by homogenizing by using standard homogenizing equipment such as the Eppenbach Homo-mixer. In the case where the ascorbic acid dissolved in the nonaqueous polar organic solvent forms the continuous phase, the nonaqueous nonpolar organic solvent is emulsified into the ascorbic acid mixture at room temperature using homogenization.

The ascorbic acid containing compositions are then applied to skin.

The Method

In the method of the invention the ascorbic acid containing compositions are applied to mammalian, in particular human, skin. The compositions may be applied once, twice, or more times per day depending on the activities the particular individual is engaged in. For example, an individual engaging in normal workday activities may wish to apply the compositions twice a day, once in the morning, and once in the evening, in conjunction with normal grooming. On the other hand, if the individual plans outdoor activities such as sunbathing and athletics, the compositions may be applied prior to, and during, such activities, much like a sunscreen composition is applied periodically during the day. Preferably, the compositions are used to reduce sunburn cell formation on the face and neck, by applying appropriate ascorbic acid compositions to the face and neck areas. However, the ascorbic acid compositions may also be applied to the entire body, particularly areas which are not covered by clothing, such as the arms, neck, and lower legs.

It has been found the application of ascorbic acid containing compositions in this manner significantly reduces the number of sunburn cells which are formed upon exposure to UV, particularly UVB radiation. Generally, the quantitation of sunburn cell formation is determined by obtaining slide preparations of skin cells according to well known histological techniques. The slides are then stained with hematoxylin-eosin, and the number of dyskeratotic cells per high power field (generally 100x magnification) is counted. Generally a number of high power fields are counted, for example 25 to 100 high power fields per sample, to ensure relability of results. Mean sunburn cell counts from skin areas treated with the ascorbic acid containing compostion are compared with the sunburn cell counts from untreated skin and placebo treated skin are compared.

It has been found that the the method of the invention provides a 10–95%, preferably 20–70%, more preferably 30–60% reduction in the number of sunburn cells formed when compared to untreated skin which is exposed to the same degree of UV radiation.

The invention will be described in connection with the following examples which are set forth for the purposes of illustration only.

EXAMPLE 1

An ascorbic acid-containing Formula (1) and Placebo (2) were prepared as follows:

|  | w/w % | |
|---|---|---|
|  | 1 | 2 |
| L-ascorbic acid | 10.6 | — |
| Glycerine | 35.3 | 35.4 |
| PEG-6 | 24.0 | 24.0 |
| Dimethicone copolyol | 1.05 | 2.1 |
| Cyclomethicone | 17.3 | 26.8 |
| Cetyl dimethicone copolyol | 1.0 | 1.0 |
| Trihydroxystearin | 1.7 | 1.7 |
| Trimethylsiloxysilicate/dimethicone (50:50) | 8.0 | 8.0 |
| Benzyl alcohol | 1.0 | 1.0 |

For Formula 1, the glycerine was heated to a temperature of 100° C. The ascorbic acid was added to the glycerine while maintaining the temperature at 100° C., while stirring until dissolved. The solution was then put into an ice water bath until the mixture cooled to room temperature. The mixture was a clear solution. The mixture was then heated back up to 100° C., and the PEG-6 was added to the hot mixture with stirring. The mixture was then put into an ice water bath again until cooled to room temperature.

The remaining ingredients were separately mixed, yielding a nonpolar solvent phase, and the ascorbic acid/glycerine/PEG-6 mixture was dispersed into the nonpolar solvent phase by homogenizing using an Eppenbach Homo-mixer.

For Placebo 2, the identical procedure was followed except that ascorbic acid was not added to the composition and the cyclomethicone level was slightly increased to replace the ascorbic acid.

EXAMPLE 2

The test subjects were five healthy caucasian adults between the ages of 19 and 47 years classified has having skin types I, II, or III as follows:

Type I: always burns easily, never tans (sensitive)

Type II: always burns easily; tans minimally (sensitive)

Type III: burns moderately; tans gradually—normal skin (light brown)

For each subject two test sites of 5×10 cm. were selected on the mid-back region and marked with gentian violet pens. Formula 1 (from Example 1) was applied to the first test site and Formula 2 (from Example 1) to the second test site, once daily for ten consecutive days at a dose of 2 mg/cm². A laboratory technician applied all samples by rubbing into the test site with a finger cot. Subjects were given detailed instructions to avoid direct exposure to sunlight and minimize any incidental UV exposure for the entire duration of the study.

For each subject, ten to fifteen minutes following the last application of product on day 10, the Minimal Erythemal Dose (MED) was determined in each of the two test sites as well as in an adjoining area of normal untreated skin. MED was measured according to the standardized procedures set forth in the Federal Register, Volume 58, No. 90, Wednesday, May 12, 1993, Subpart D, Sections 352.70–352.77. A bank of four 20 inch fluorescent FS20 bulbs (which have wavelengths predominantly in the UVB region of 290–320 nm.) were filtered with 0.15 mm. thick cellulose acetate to remove any incidental UVC (which has a wavelength of less than 290 nm.). The MED was determined by administering a series of time exposures at a source to skin distance of 12 inches, in 25% increments to small subsites within the treated area using a template with punched out holes for delivering the intended dose. The MED (the shortest exposure required to produce a barely visible response) in each site was evaluated and recorded 20±2 hours after exposure.

After evaluation and recording of MED, a shave biopsy of about 4×4 mm. was obtained from a subsite within each of the two treated areas, as well as from the untreated, normal, irradiated skin, following injection of a local anesthetic (xylocaine). The biopsied subsites in the two untreated areas and the untreated skin were all irradiated or exposed to the same dose of UVB as previously used, in particular 2 ml/cm$^2$. Each specimen was fixed in 10% formalin.

The fixed specimens were processed routinely, embedded in paraffin and then sectioned and stained with hematoxylin-eosin. The numbers of sunburn cells (SBC's) were determined in at least 16 sections at 50 micron intervals. A minimum of 74 high power fields (100x magnification) were counted from each biopsy and the average was determined. All specimens were counted in a blinded manner by the investigator.

The MED in each test site is summarized in the following table I:

I.
Minimal Erythemal Dose (MED) (measured in millijoules/cm$^2$)

| Subject No. | Site A* | Site P* | Site C* |
| --- | --- | --- | --- |
| 1 | 102.0 | 81.6 | 81.6 |
| 2 | 81.6 | 81.6 | 65.3 |
| 3 | 41.5 | 41.5 | 41.5 |
| 4 | 52.0 | 52.0 | 41.5 |
| 5 | 102.0 | 102.0 | 102.0 |

*Site A: Formula 1
Site P: Formula 2
Site C: Normal untreated skin

The mean number of sunburn cells (SBC's) for each subject is set forth below in Table II.

II.
Mean Number of SBC's Per High Power Field

| Subject No. | Site A* | Site P* | Site C* |
| --- | --- | --- | --- |
| 1 | 0.56 | 0.90 | 1.01 |
| 2 | 0.05 | 0.17 | 0.44 |
| 3 | 2.01 | 2.14 | 3.38 |
| 4 | 0.44 | 0.59 | 0.90 |
| 5 | 0.45 | 1.16 | 1.11 |
| Grand Mean (X) | 0.70 | 0.99 | 1.37 |

*Site A: Formula 1
Site P: Formula 2
Site C: Normal untreated skin

Conclusion: The MED in normal untreated skin ranged from 41.5 to 102.0 mj/cm$^2$. It does not appear that Formula 1 produced any effect different from Formula 2 with respect to MED. However, with respect to sunburn cells, Formula 1 (active) produced about a 50% reduction in the number of sunburn cells when compared with normal, untreated skin, and a significant reduction in the number of sunburn cells when compared to Formula 2. Thus, the application of ascorbic acid containing compositions to skin prior to exposure to UV radiation reduces the formation of sunburn cells in mammalian skin.

While the invention has been described in connection with the preferred embodiment, it is not intended to limit the scope of the invention to the particular form set forth, but, on the contrary, it is intended to cover such alternatives, modifications and equivalents as may be included within the spirit and scope of the invention as defined by the appended claims.

We claim:

1. A method for reducing the formation of sunburn cells in human skin exposed to ultraviolet radiation, comprising applying a composition containing an amount of ascorbic acid sufficient to reduce the formation of sunburn cells in human skin, to the skin prior to exposure to ultraviolet radiation.

2. The method of claim 1 wherein the ultraviolet radiation is ultraviolet B radiation.

3. The method of claim 1 wherein the composition contains about 0.01–25% by weight of the total composition, of ascorbic acid.

4. The method of claim 3 wherein the composition contains about 10–95% by weight of the total composition, of a polar organic solvent.

5. The method of claim 3 wherein the composition contains about 0.1–30% by weight of the total composition, of a surfactant.

6. The method of claim 3 wherein the composition contains 1–50% by weight of the total composition, of a nonvolatile oil.

7. The method of claim 3 wherein the composition contains, by weight of the total composition:
   0.1–25% of ascorbic acid,
   10–95% of a polar organic solvent,
   0.1–30% of a surfactant; and
   1–50% of a nonvolatile oil.

8. The method of claim 1 wherein, relative to untreated skin, there is a 10–95% reduction in the number of sunburn cells by applying a composition containing ascorbic acid to the the skin prior to exposure to ultraviolet radiation.

9. The method of claim 8 wherein, relative to untreated skin, there is a 20–70% reduction in the number of sunburn cells when applying a composition containing ascorbic acid to the skin prior to exposure to ultraviolet radiation.

10. The method of claim 9 wherein, relative to untreated skin, there is a 30–60% reduction in the number of sunburn cells when applying a composition containing stabilized ascorbic acid to the skin prior to exposure to ultraviolet radiation.

11. The method of claim 1 wherein the cosmetic composition is applied at least once a day.

12. The method of claim 1 wherein the cosmetic composition is applied at least twice a day.

13. The method of claim 1 wherein the cosmetic composition is applied prior to engaging in outdoor activities.

14. The method of claim 1 wherein the skin is facial skin.

15. The method of claim 14 wherein the skin is on the neck, arms, or legs.

16. The method of claim 1 wherein the composition is a cosmetic composition.

17. The method of claim 1 wherein the composition is a pharmaceutical composition.

* * * * *